US006221840B1

(12) United States Patent
Podolsky

(10) Patent No.: US 6,221,840 B1
(45) Date of Patent: *Apr. 24, 2001

(54) INTESTINAL TREFOIL PROTEINS

(75) Inventor: Daniel K. Podolsky, Wellesley Hills, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/631,469

(22) Filed: Apr. 12, 1996

Related U.S. Application Data

(63) Continuation-in-part of application No. 08/191,352, filed on Feb. 2, 1994, now abandoned, which is a continuation-in-part of application No. 08/037,741, filed on Mar. 25, 1993, now abandoned, which is a continuation-in-part of application No. 07/837,192, filed on Feb. 13, 1992, now abandoned, which is a continuation-in-part of application No. 07/655,965, filed on Feb. 14, 1991, now abandoned.

(51) Int. Cl.$^7$ .................................................. A61K 38/16
(52) U.S. Cl. ...................................... 514/12; 514/8; 514/2
(58) Field of Search .................. 435/69.1, 91, 172.3, 435/320.1, 235.1; 536/27, 23.5; 530/300; 514/2, 8, 12; 935/9, 10, 23, 55, 60, 70, 72

(56) References Cited

U.S. PATENT DOCUMENTS 4,370,317   1/1983   Jorgensen et al. .

FOREIGN PATENT DOCUMENTS

WO 92/14837   9/1992   (WO) .
WO 96/06861   3/1996   (WO) .

OTHER PUBLICATIONS

Falk et al., "Expression of a Human α–1,¾–Fucosyltransferase in the Pit Cell Lineage of FVB/N Mouse Stomach Results in Production of Le$^b$–Containing . . . ", Proc. Natl. Academic Sci. USA, 92:1515–1519, 1995.
Jakowlev et al., "Sequence of the pS2 mRNA Induced by Estrogen in the Human Breast Cancer Cell Line MCF–7", Nucleic Acis Res., 12:2861, 1984.
Jeffrey et al., "Spasmolytic Polypeptide: A Trefoil Peptide Secreted by Rat Gastic Mucous Cells", Gastroenterology, 106:336, 1994.
Jorgensen et al., Regulatory Peptides, 3:231, 1982.
Mori et al., "Identification of a Polypeptide Secreted by Human Breast Cancer Cells (MCF–7) as the Human Estrogen–Responsive Gene (pS2) Product", Biochem. Biophys. Res. Comm. 155:366, 1988.
Okayasu et al., "A Novel Method in the Induction of Reliable Experimental Acute and Chronic Ulcerative Colitis in Mice", Gastroenterology, 98:694, 1990.
Podolsky et al., "Latent Transformed Growth–Inhibiting Factor in Human Malignant Effusions", Cancer Research 48:418, 1988.
Podolsky et al., "Demonstration of Distinct Subpopulations Defined by Mucin–Specific Monoclonal Antibodies" J. Clin. Invest., 77:1263, 1986.
Sands et al., "The Trefoil Peptide Family", Annual Review of Physiology, 58:253–273, 1996.
Suemori et al., "Identification and Characterization of Rat Intestinal Trefoil Factor: Tissue– and Cell–Specific Member of the Trefoil Protein Family", Proc. Natl. Acad. Science USA, 88:11017, 1991.
Thim et al., Biochem. Biophys. Acta., 827:410, 1985.
Podolsky et al., Identification of Human Intestinal Trefoil Factor, Journal of Biological Chemistry, vol. 268, No. 9, 6694–6702 (1993).
Babyatsky et al., Trefoil Peptides Protect Against Ethanol and Indomethacin Induced Gastric Injury in Rats, Gastroenterology, vol. 106, No. 4, A43, (1994).
Kindon et al., "Trefoil Peptide Protection of Intestinal . . . " Gastroenterology 109:516–523 1995.
Lazar et al. Mol. Cell Biol. 8(3):1247–52, Mar. 1988.*
Burgess et al. J. Cell Biol. 111:2129–38, Nov. 1990.*
"Peptide Hormones", edited by J.A. Parson, published by University Park Press (Baltimore), see Chapter 1, pp. 1–7, Jun. 1976.*

* cited by examiner

*Primary Examiner*—Patricia A. Duffy
(74) *Attorney, Agent, or Firm*—Fish & Richardson P.C.

(57) ABSTRACT

Intestinal trefoil factors and nucleic acids encoding intestinal trefoil factors are disclosed. The intestinal trefoil factors disclosed are resistent to destruction in the digestive tract and can be used for the treatment of peptic ulcer diseases, inflammatory bowel diseases and other insults.

17 Claims, 9 Drawing Sheets

```
gaagtttgcg tgctgcc                                                          17
atg gag acc aga gcc ttc tgg ata acc ctg ctg gtc ctg gtt                     62
gct ggg tcc tcc tgc aaa gcc cag gaa ttt gtt ggc cta tct cca                 107
agc caa tgt atg gcg cca aca aat gtc agg gtg gac tgt aac tac                 152
ccc act gtc aca gag cag tgt aac aac cgt ggt tgc tgt ttt                     197
gac tcc agc atc cca aat gtg ccc tgg tgc ttc aaa cct ctg caa                 242
gag aca gaa tgt aca ttt                                                     260
tgaagctgtc caggctccag gaagggagct ccacaccctg gactcttgct                      310
gatggtagtg gcccaggta acactcaccc ctgatctgct ccctcgcgcc                       360
ggccaatata ggagctggga gtccagaaga ataaagacct tacagtcagc                      410
acaaggctgt tctaattgcg g                                                     431
(SEQ ID NO: 1)
```

FIG. 1

```
Met Glu Thr Arg Ala Phe Trp Ile Thr Leu Leu Val Leu Val
                 5                  10              15
Ala Gly Ser Ser Cys Lys Ala Gln Glu Phe Val Gly Leu Ser Pro
                20                  25              30
Ser Gln Cys Met Ala Pro Thr Asn Val Arg Val Asp Cys Asn Tyr
                35                  40              45
Pro Thr Val Thr Ser Glu Gln Cys Asn Asn Arg Gly Cys Cys Phe
                50                  55              60
Asp Ser Ser Ile Pro Asn Val Pro Trp Cys Phe Lys Pro Leu Gln
                65                  70              75
Glu Thr Glu Cys Thr Phe
                80

(SEQ ID NO: 2)
```

FIG. 2

```
rITF  METRAFWITLLLVLVAGSSCKAQEFVGLSPSQCHAPTNVRVDCNYPTVTSEQCNNRGCC
pS2   ---------------------EAQ-------TETCTVAPRERQNCGFPGVTPSQCANKGCC
PSP   ---------------------EKPAACRCSRQDPKN-RVNCGFPGITSDQCFTSGCC rITF  FDSSIPNVPWCFK-----PLQ----ETECT------F   (SEQ ID NO: 1)
pS2   FDDTVRGVPWCFY-----PNTIDVPPEECE------F   (SEQ ID NO: 15)
PSP   FDSQVPGVPWCFK-----PLP----AQESEECVMEV   (SEQ ID NO: 16)
```

FIG. 3

(SEQ ID NO: 15)

(SEQ ID NO: 16)

(SEQ ID NO: 17)

```
1   gatgctgggctggtcctgcctgctgtcctccagctctgctgtcctgaggagtacgtgggcct
    ----+----+----+----+----+----+----+----+----+----+----+----+    60
    M  L  G  L  V  L  A  L  L  S  S  S  A  E  E  Y  V  G  L 61  gtctgcaaccagtgtgccgtgccggccaaggacagggtggactgcggctaccccatgt
    ----+----+----+----+----+----+----+----+----+----+----+----+   120
    S  A  N  Q  C  A  V  P  A  K  D  R  V  D  C  G  Y  P  H  V 121 cacccccaaggagtgcaacaaccgggctgctgctttgactcccaggatccctgagtgcc
    ----+----+----+----+----+----+----+----+----+----+----+----+   180
    T  P  K  E  C  N  N  R  G  C  C  F  D  S  R  I  P  G  V  P 181 ttggtgtttcaagcccctgcaggaagcagagaatgcacctt ctgaggcacctccagctg
    ----+----+----+----+----+----+----+----+----+----+----+----+   240
    W  C  F  K  P  L  Q  E  A  E  C  T  F  *

241 cccctgggatgcaggctgagcaccct tgcccggctgtgattgctgcaggcactgttcat
    ----+----+----+----+----+----+----+----+----+----+----+----+   300

301 ctcagttttctgtccctttgctccc cggcaagctttctgctgaaagttcatatctggagc
    ----+----+----+----+----+----+----+----+----+----+----+----+   360

361 ctgatgtcttaacgaataaaggtcccatgctccacccgAAAAA          SEQ ID NO:3
    ----+----+----+----+----+----+----+----+             SEQ ID NO:18
                                       400
```

FIG. 6

INTESTINAL TREFOIL PROTEINS

This application is a continuation-in-part of U.S. Ser. No. 08/191,352, filed Feb. 2, 1994, now abandoned which is a continuation of U.S. Ser. No. 08/037,741, filed Mar. 25, 1993, now abandoned which is a continuation of U.S. Ser. No. 07/837,192, filed Feb. 13, 1992, now abandoned which is a continuation-in-part of U.S. Ser. No. 07/655,965, filed Feb. 14, 1991 now abandoned.

BACKGROUND

The field of the invention is peptides useful for treatment of disorders of the digestive system.

Jørgensen et al. (1982, Regulatory Peptides 3:231) describe a porcine pancreatic peptide, pancreatic spasmolytic peptide (PSP). PSP was found to inhibit "gastrointestinal motility and gastric acid secretion in laboratory animal after parenteral as well as oral administration." It was suggested that "if the results in animal experiments can be confirmed in man, PSP may possess a potential utility in treatment of gastroduodenal ulcer diseases."

SUMMARY OF THE INVENTION

In a first aspect, the invention features a purified nucleic acid encoding an intestinal trefoil factor (ITF).

In preferred embodiments, the intestinal trefoil factor is mammalian intestinal trefoil factor, preferably human, rat, bovine, or porcine intestinal trefoil factor. In another preferred embodiment, the purified nucleic acid encoding an intestinal trefoil factor is present within a vector.

In a related aspect, the invention features a cell that includes a vector encoding an intestinal trefoil factor.

In another related aspect, the invention features a substantially pure intestinal trefoil factor. In a preferred embodiment, the polypeptide is detectably labelled. In a related aspect, the invention features a therapeutic composition that includes an intestinal trefoil factor and a pharmacologically acceptable carrier.

In another aspect, the invention features a monoclonal antibody which preferentially binds (i.e., forms an immune complex with) an intestinal trefoil factor. In a preferred embodiment, the monoclonal antibody is detectably labelled.

In a related aspect, the invention features a method for detecting human intestinal trefoil factor in a human patient. The method includes the steps of contacting a biological sample obtained from the patient with a monoclonal antibody which preferentially binds intestinal trefoil factor, and detecting immune complexes formed with the monoclonal antibody. In preferred embodiments the biological sample is an intestinal mucosal scraping, or serum.

In a related aspect, the invention features a method for treating digestive disorders in a human patient, which method involves administering to the patient a therapeutic composition that includes an intestinal trefoil factor and a pharmacologically acceptable carrier.

In another aspect, the invention features a method for detecting binding sites for intestinal trefoil factor in a patient. The method involves contacting a biological sample obtained from the patient with the factor, and detecting the factor bound to the biological sample as an indication of the presence of the binding sites in the sample. By "binding sites," as used herein, is meant any antibody or receptor that binds to an intestinal trefoil factor protein, factor, or analog. The detection or quantitation of binding sites may be a useful reflection of abnormalities of the gastrointestinal tract.

In another aspect, the invention features substantially pure trefoil factor. In preferred embodiments, the intestinal trefoil factor is human, porcine, or bovine trefoil factor.

By "intestinal trefoil factor" ("ITF") is meant any protein that is substantially homologous to rat intestinal trefoil factor (FIG. 2; SEQ ID NO.:2) and which is expressed in the large intestine, small intestine, or colon to a greater extent than it is expressed in tissues other than the small intestine, large intestine, or colon. Also included are: allelic variations; natural mutants; induced mutants; proteins encoded by DNA that hybridizes under high or low stringency conditions to ITF encoding nucleic acids retrieved from naturally occurring material; and polypeptides or proteins retrieved by antisera to ITF, especially by antisera to the active site or binding domain of ITF. The term also includes other chimeric polypeptides that include an ITF.

The term ITF also includes analogs of naturally occurring ITF polypeptides. Analogs can differ from naturally occurring ITF by amino acid sequence differences or by modifications that do not affect sequence, or by both. Analogs of the invention will generally exhibit at least 70%, more preferably 80%, more preferably 90%, and most preferably 95% or even 99%, homology with all or part of a naturally occurring ITF sequence. The length of comparison sequences will generally be at least 8 amino acid residues, usually at least 20 amino acid residues, more usually at least 24 amino acid residues, typically at least 28 amino acid residues, and preferably more than 35 amino acid residues. Modifications include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes that affect glycosylation derived from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine. Analogs can differ from naturally occurring ITF by alterations of their primary sequence. These include genetic variants, both natural and induced. Induced mutants may be derived by various techniques, including random mutagenesis of the encoding nucleic acids using irradiation or exposure to ethanemethylsulfate (EMS), or may incorporate changes produced by site-specific mutagenesis or other techniques of molecular biology. See, Sambrook, Fritsch and Maniatis (1989), *Molecular Cloning: A Laboratory Manual* (2d ed.), CSH Press, hereby incorporated by reference. Also included are analogs that include residues other than naturally occurring L-amino acids, e.g., D-amino acids or non-naturally occurring or synthetic amino acids, e.g., β or γ amino acids.

In addition to substantially full-length polypeptides, the term ITF, as used herein, includes biologically active fragments of the polypeptides. As used herein, the term "fragment," as applied to a polypeptide, will ordinarily be at least 10 contiguous amino acids, typically at least 20 contiguous amino acids, more typically at least 30 contiguous amino acids, usually at least 40 contiguous amino acids, preferably at least 50 contiguous amino acids, and most preferably at least 60 to 80 or more contiguous amino acids in length. Fragments of ITF can be generated by methods known to those skilled in the art. The ability of a candidate fragment to exhibit a biological activity of ITF can be assessed by methods known to those skilled in the art. Also included in the term "fragment" are biologically active ITF polypeptides containing amino acids that are normally removed during protein processing, including additional amino acids that are not required for the biological activity of the polypeptide, or including additional amino acids that result from alternative mRNA splicing or alternative protein processing events.

An ITF polypeptide, fragment, or analog is biologically active if it exhibits a biological activity of a naturally occurring ITF, e.g., the ability to alter gastrointestinal motility in a mammal.

The invention also includes nucleic acid sequences, and purified preparations thereof, that encode the ITF polypeptides described herein. The invention also includes antibodies, preferably monoclonal antibodies, that bind specifically to ITF polypeptides.

As used herein, the term "substantially pure" describes a compound, e.g., a nucleic acid, a protein, or a polypeptide, e.g., an ITF protein or polypeptide, that is substantially free from the components that naturally accompany it. Typically, a compound is substantially pure when at least 60%, more preferably at least 75%, more preferably at least 90%, and most preferably at least 99%, of the total material (by volume, by wet or dry weight, or by mole percent or mole fraction) in a sample is the compound of interest. Purity can be measured by any appropriate method, e.g., in the case of polypeptides, by column chromatography, polyacrylamide gel electrophoresis, or HPLC analysis.

By "isolated DNA" is meant DNA that is free of the genes which, in the naturally-occurring genome of the organism from which the given DNA of the invention is derived, flank the DNA. The term "isolated DNA" thus encompasses, for example, cDNA, cloned genomic DNA, and synthetic DNA. A "purified nucleic acid", as used herein, refers to a nucleic acid sequence that is substantially free of other macromolecule (e.g., other nucleic acids and proteins) with which it naturally occurs within a cell. In preferred embodiments, less than 40% (and more preferably less than 25%) of the purified nucleic acid preparation consists of such other macromolecule. "Homologous", as used herein, refers to the subunit sequence similarity between two polymeric molecules, e.g., between two nucleic acid molecules, e.g., two DNA molecules, or two polypeptide molecules. When a subunit position in both of the molecules is occupied by the same monomeric subunit, e.g., if a position in each of two DNA molecules is occupied by adenine, then they are homologous at that position. The homology between two sequences is a direct function of the number of matching or homologous positions, e.g., if half, e.g., 5 of 10, of the positions in two compound sequences are homologous then the two sequences are 50% homologous; if 90% of the positions, e.g., 9 of 10, are matched or homologous the two sequences share 90% homology. By way of example, the DNA sequences 3'ATTGCC'5 and 3'TATGGC'5 share 50% homology. By "substantially homologous" is meant largely but not wholly homologous.

The ITF proteins of the invention are resistant to destruction in the digestive tract, and can be used for treatment of peptic ulcer diseases, inflammatory bowel diseases, and for protection of the intestinal tract from injury caused by insults such as radiation injury or bacterial infection. An ITF protein, fragment, or analog can also be used to treat neoplastic cancer.

In general, trefoil proteins, including ITF, are useful for the treatment of disorders of and damage to the alimentary canal, including the mouth, esophagus, stomach, and large and small intestine.

One of the most common bacterial infections is caused by *Helicobacter pylori* (*H. pylori*), which leads to active, chronic gastritis and frequently to associated syndromes such as duodenal ulcer, gastric ulcer, gastric cancer, MALT lymphoma, or Menetrier's syndrome. Eradication of *H. pylori* has been shown to reduce the recurrence of duodenal and gastric ulcers. Furthermore, it has been postulated that widespread treatment of *H. pylori* will reduce the incidence of gastric carcinoma, which is the second leading cause of cancer related death world-wide.

Long-standing gastritis associated with *H. pylori* infection is often associated with the expression of intestinal-like features in the gastric mucosa. This condition, referred to as intestinal metaplasia (IM), may signal an increased risk of gastric cancer. The etiology of IM is unclear; it could represent a mutational adaptation or defense against *H. pylori* infection. For example, the metaplastic mucosa may produce mucus or other substances that create an environment that is hostile to *H. pylori*. ITF can be used in the treatment of *H. pylori* infection and conditions associated with *H. pylori* infection (e.g., ulcers, gastric carcinoma, non-ulcer dyspepsia, gastritis, and esophageal lesions associated with gastro-esophageal reflux disease). ITF is useful for treatment of these conditions because of its generally protective effect on the gastrointestinal tract. In addition, ITF promotes the maintenance of mucosal integrity. ITF can be used to inhibit adhesion to or colonization of the mucosa by *H. pylori*. In this application ITF or fragments or variants thereof which inhibit adhesion or colonization of the mucosa by *H. pylori* are useful. Such molecules can be identified using assays known to those skilled in the art, including the *H. pylori* binding assay described below.

ITF may also be used promote healing of tissues damaged by conditions associated with *H. pylori* infection. In this regard, it is important that addition of trefoil proteins to wounded monolayers of confluent intestinal epithelial cells increases the rate of epithelial cell migration into the wound. This effect is enhanced by concomitant addition of mucin glycoproteins, the other dominant product of goblet cells.

Just as ITF can be used to protect other parts of the gastro-intestinal tract or alimentary canal, such as the intestine, it can be used to protect the mouth and esophagus from damage caused by radiation therapy or chemotherapy. ITF can also be used to protect against and/or to treat damage caused by alcohols or drugs generally.

Members of the trefoil family, including ITF, can be used in the treatments discussed above. Skilled artisans may review these proteins in Sands et al. (1996, Ann. Rev. Physiol. 58:253–273). As stated above, the invention encompasses biologically active fragments of the trefoil proteins. Fragments that retain the trefoil structure (i.e., the three loop structure) or that lie within regions of the protein that are highly conserved may prove particularly useful. Thus, portions of ITF from about the first cys involved in a disulfide bond of the three loop structure to about the last cys involved in a disulfide bond of the three loop structure.

Variants of a selected trefoil protein are least 60%, preferably at least 75%, more preferably at least 90%, and most preferably at least 95% identical to the selected trefoil protein, preferably a human trefoil protein, more preferably human ITF.

The term "identical," as used herein in reference to polypeptide or DNA sequences, refers to the subunit sequence identity between two molecules. In the case of amino acid sequences that are less than 100% identical to a reference sequence, the non-identical positions are preferably, but not necessarily, conservative substitutions for the reference sequence. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Sequence identity is typically measured using sequence analysis software such as the Sequence Analysis Software Package of the Genetics Computer Group at the University of Wisconsin (Biotechnology Center, 1710 University Avenue, Madison, Wis. 53705), and the default parameters specified therein.

A variant of a selected trefoil protein preferably has the amino acids present in the naturally-occurring form of the selected trefoil protein at the more highly conserved amino acid positions of the protein. Thus, a variant of human ITF preferably is identical to naturally-occurring human ITF at all or nearly all of the more highly conserved positions. Sequence conservation among trefoil proteins is evident in Table 1 of Sands et al. (supra) which can be used by those skilled in the art to identify more conserved residues. The invention features a method for the treatment of lesions in the alimentary canal of a patient by administering to the patient at least one trefoil peptide, or a biologically active fragment thereof. The lesions typically occur in the mucosa of the alimentary canal, and may be present in the mouth, esophagus, stomach, or intestine of the patient. The lesions can be caused in several ways. For example, the patient may be receiving radiation therapy or chemotherapy for the treatment of cancer. These treatments typically cause lesions in the mouth and esophagus of the patient. Skilled artisans will recognize that it may be useful to administer the proteins of the invention to the patient before such treatment is begun. Alternatively, the lesions can be caused by: (1) any other drug, including alcohol, that damages the alimentary canal, (2) accidental exposure to radiation or to a caustic substance, (3) an infection, or (4) a digestive disorder including but not limited to non-ulcer dyspepsia, gastritis, peptic or duodenal ulcer, gastric cancer, MALT lymphoma, Menetrier's syndrome, gastro-esophageal reflux disease, and Crohn's disease. The peptide that is administered may be any peptide in the trefoil family, such as intestinal trefoil peptide (ITF), spasmolytic peptide (SP), and pS2. For the treatment of human patients it is expected that the peptide will be expressed by a human gene. However, eucaryotic trefoil peptides, such as those cloned from the rat and mouse genomes may also prove effective. These peptides may be isolated from a naturally occurring source or synthesized by recombinant techniques. It is expected that the typical route of administration will be oral. Determining other routes of administration, and the effective dosage are well within the skills of ordinary artisans and will depend on many factors known to these artisans. The trefoil proteins may be administered singly, in combination with one another, and/or in combination with mucin glycoprotein preparations.

"Treatment of lesions" encompasses both the inhibition of the formation of lesion and the healing of lesions already formed. Biologically active fragments and variants of a trefoil protein, particularly ITF, which promote healing of lesions or inhibit the formation of lesions are useful in the treatments of the invention.

Other features and advantages of the invention will be apparent from the following description of the preferred embodiments thereof, and from the claims.

BRIEF DESCRIPTION OF THE DRAWINGS

FIG. 1 is a depiction of the nucleotide sequence of rat trefoil factor (SEQ ID NO.:1).

FIG. 2 is a depiction of the deduced amino acid sequence of rat trefoil factor (SEQ ID NO.:2).

FIG. 3 is a depiction of the amino acid sequences of rat trefoil factor, pS2 protein, and pancreatic spasmolytic polypeptide (SP). The sequences are aligned to illustrate the amino acid sequence homology between the proteins. Dashes (-) indicate the insertion of spaces which optimize alignment. Bars indicate sequence identity.

FIG. 6 is a depiction of the nucleotide sequence of the human intestinal trefoil factor cDNA and the corresponding deduced amino acid sequence (SEQ ID NO.:3).

DETAILED DESCRIPTION

Purification and cloning of rITE

An inhibitor of soft agar colony formation by human breast carcinoma-derived BT-20 cells (ATTC HTB79) was isolated from cytology-positive human malignant effusions (Podolsky et al., 1988, Cancer Res. 48:418; hereby incorporated by reference). The factor also inhibited soft agar colony formation by human colon carcinoma-derived HCT15 cells (ATTC-CCL225). Inhibition was not observed for polyoma and murine sarcoma virus transformed rodent fibroblast lines. The isolated factor (transformed cell-growth inhibiting factor or TGIF) had an apparent molecular weight of 110,000 kD and appeared to consist of two 55,000 kD subunits linked by sulfhydryl bonds.

The purified protein was partially sequenced. The sequence from the amino terminal 14 amino acids was used to produce a set of degenerate oligonucleotide probes for screening of a rat intestinal epithelial cell cDNA library.

A rat intestinal cDNA library (Lambda ZAP™ II, Stratagene, La Jolla, Calif.) was produced by standard techniques (Ausubel et al., Eds., Current Protocols in Molecular Biology, John Wiley & Sons, New York, 1989) using cells purified by the method of Weisner (1973, J. Biol. Chem. 248:2536). Screening of the cDNA library with the fully degenerate oligonucleotide probe described above resulted in the selection of 21 clones. One of the clones (T3411) included a core sequence which encoded a single open reading frame. The nucleotide sequence of the open reading frame and flanking DNA is presented in FIG. 1 (SEQ ID NO.:1). The insert present in T3411 was nick translated (Ausubel et al., supra) to produce a radioactively labelled probe for Northern blot analysis of rat poly(A)$^+$ RNA. Northern analysis demonstrated that RNA corresponding to the cloned cDNA fragment was expressed in small intestine, large intestine, and kidney; no expression was detected in the lung, spleen, heart, testes, muscle, stomach, pancreas, or liver. In the tissues in which the RNA was expressed, the level was comparable to that of actin.

Figure 4A:
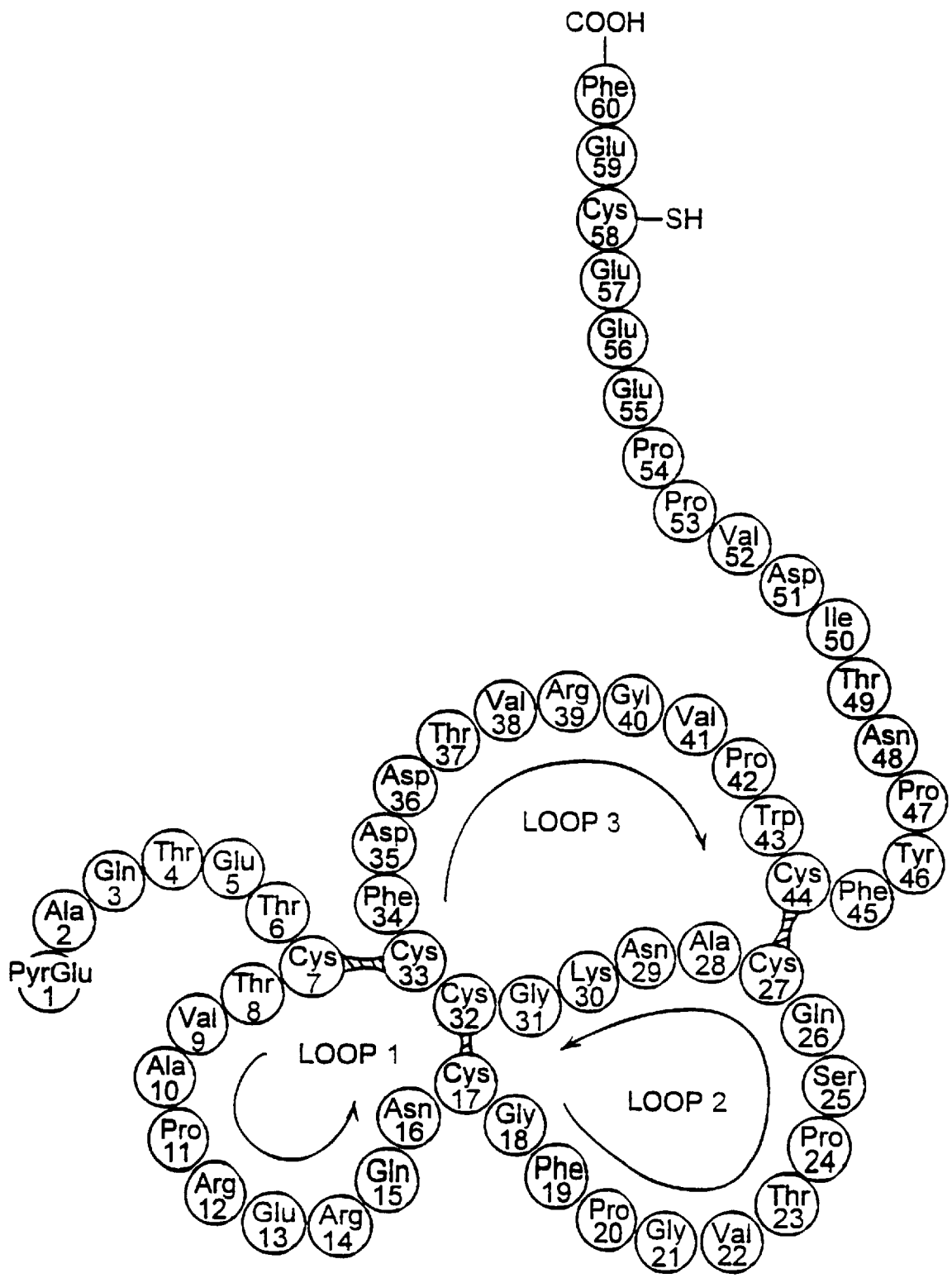
FIG. 4 depicts the disulfide bond structure proposed for pS2 (SEQ ID NO: 15) (panel A) and PSP (SEQ ID NO: 16) (panel B).
Figure 4B:
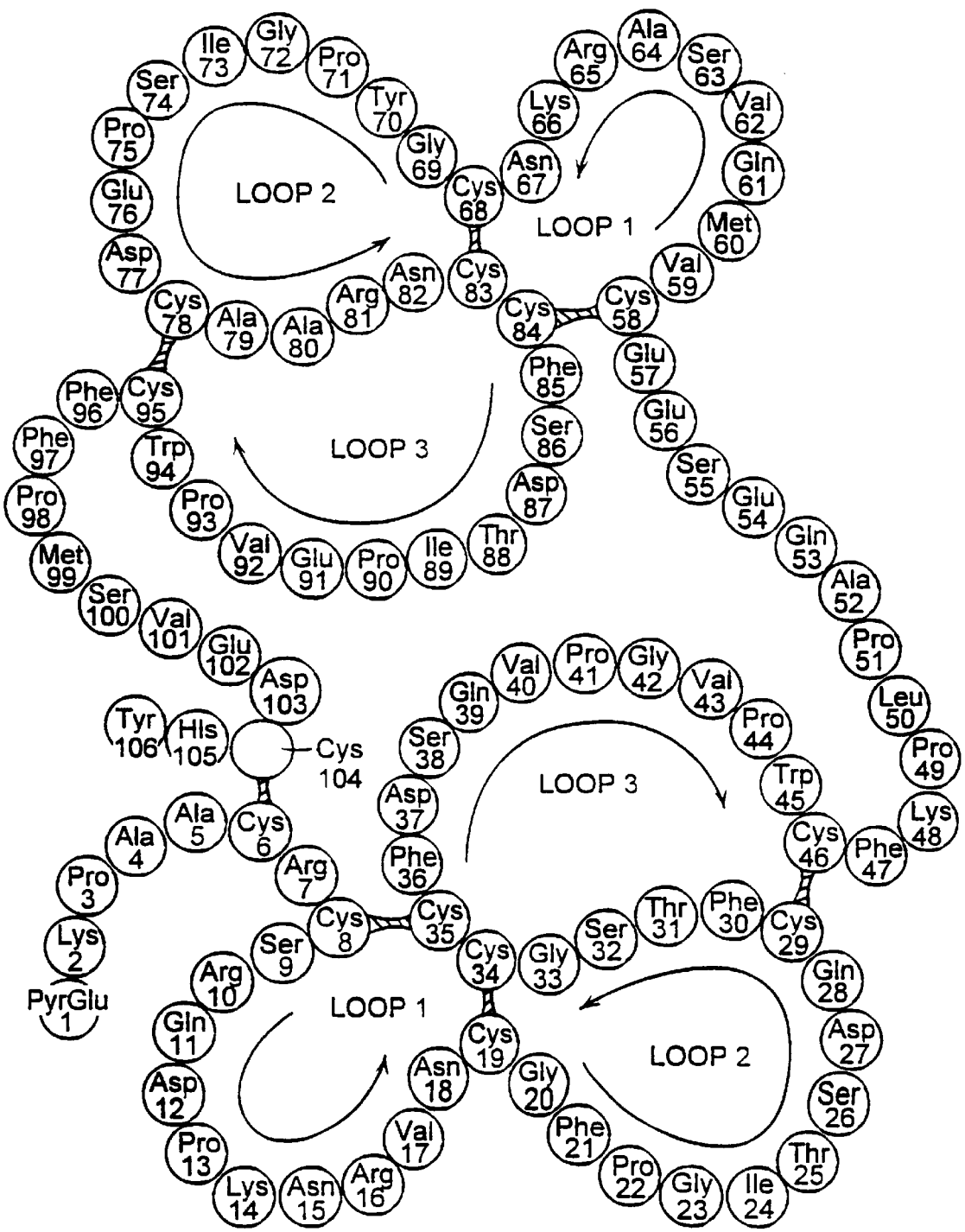
Figure 5:
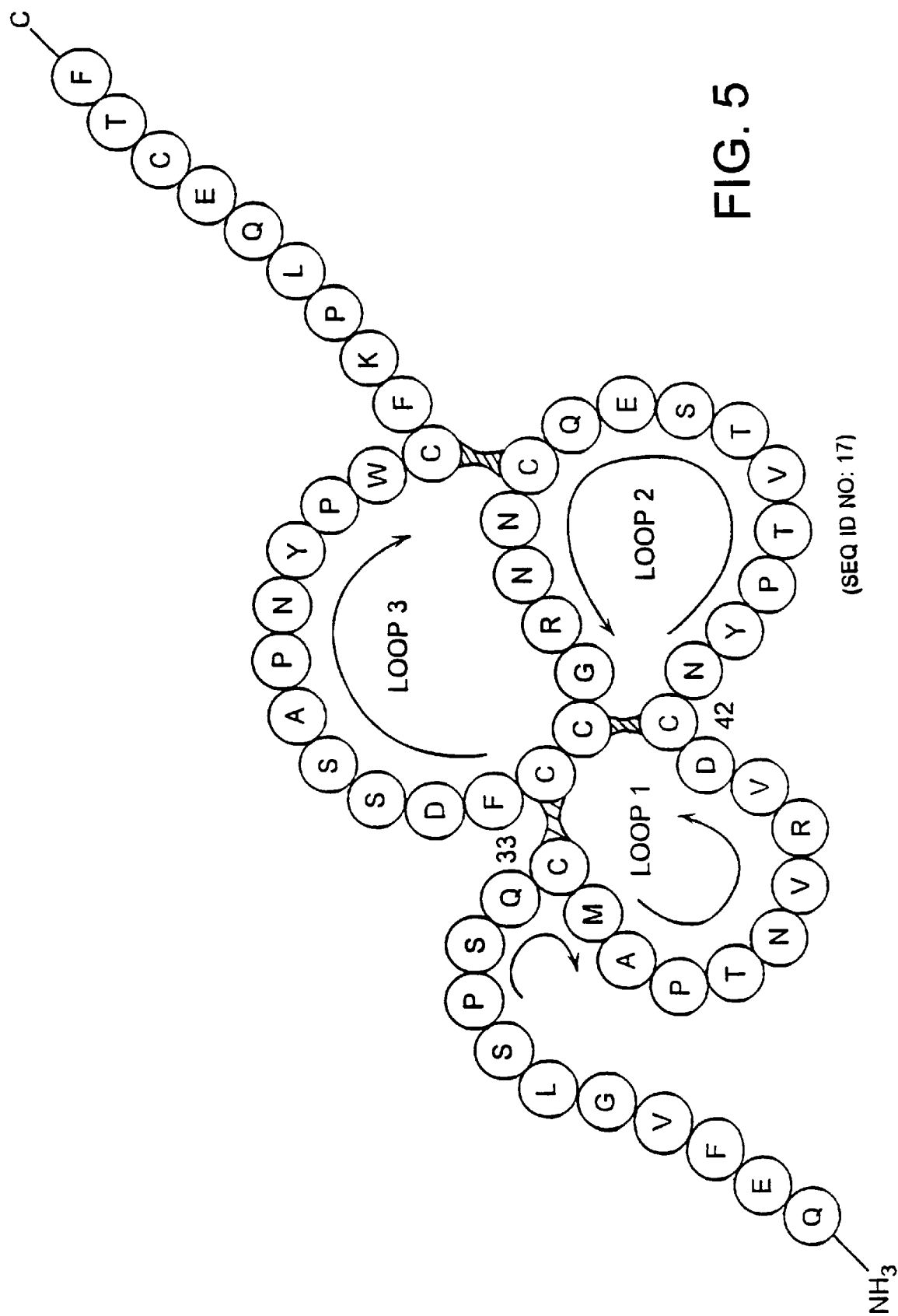
FIG. 5 is a depiction of the proposed disulfide bond structure of rat intestinal trefoil factor (SEQ ID NO.: 17).

The open reading frame of clone T3411 encoded an 81 amino acid peptide (FIG. 2; SEQ ID NO.:2). Comparison of the sequence of the encoded peptide, referred to as rat intestinal trefoil factor (rITF), to the sequence of proteins in the Genebank database revealed significant homology to human breast cancer associated peptide (pS2; Jakowlev et al., 1984, Nucleic Acids Res. 12:2861) and porcine pancreatic spasmolytic peptide (PSP; Thim et al., 1985 Biochem. Biophys. Acta. 827:410). FIG. 3 illustrates the homology between rITF, PSP and pS2. Porcine pancreatic spasmolytic factor (PSP) and pS2 are both thought to fold into a characteristic structure referred to as a trefoil. A trefoil structure consists of three loops formed by three disulfide bonds. pS2 is thought to include one trefoil (FIG. 4A), and PSP is thought to include two trefoils (FIG. 4B). The region of rITF (nucleotide 114 to nucleotide 230 which encodes cys to phe), which is most similar to PSP and pS2, includes six cysteines all of which are in the same position as the cysteines which make up the trefoil in pS2 (FIG. 3). Five of these six cysteines are in the same position as the cysteines which form the amino terminal trefoil of PSP (FIG. 3). FIG. 5 depicts the proposed disulfide bond configuration of rITF.

Based on homology to PSP and pS2 (Mori et al., 1988, Biochem. Biophys. Res. Comm. 155:366; Jakowlev et al., 1984 Nucleic Acids Res. 12:2861), rITF includes a presumptive pro-sequence (met1 to ala22) in which 12 of 22 amino acids have hydrophobic side chains.

Production of Anti-rITF Antibodies

A peptide corresponding to the carboxy-terminal 21 amino acids of rITF was synthesized and coupled to bovine serum albumin (BSA). This conjugate (and the unconjugated peptide) was used to raise polyclonal antibodies in rabbits. All procedures were standard protocols such as those described in Ausubel et al. (supra). The anti-rITF antibodies were used in an indirect immunoflouresce assay for visualization of rITF in rat tissues. Cryosections of rat tissues were prepared using standard techniques, and fluorescein labelled goat anti-rabbit monoclonal antibody (labelled antibodies are available from such suppliers Kirkegaard and Perry Laboratories, Gaithersberg, Md.; and Bioproducts for Science, Inc., Indianapolis, Ind.) was used to detect binding of rabbit anti-rITF antibodies. By this analysis rITF appears to be present in the globlet cells of the small intestine but not in the stomach or the pancreas.

Cloning of Human Intestinal Trefoil Factor

DNA encoding the rat intestinal trefoil factor can be used to identify a cDNA clone encoding the human intestinal trefoil factor (hITF). This can be accomplished by screening a human colon cDNA library with a probe derived from rITF or with a probe derived from part of the hITF gene. The latter probe can be obtained from a human colon or intestinal cDNA using the polymerase chain reaction to isolate a part of the hITF gene. This probe can then serve as a specific probe for the identification of clones encoding all of the hITF gene.

Construction of a cDNA Library

A human colon or intestinal cDNA library in λgtlO or λgtll, or some other suitable vector is useful for isolation of hITF. Such libraries may be purchased (Clontech Laboratories, Palo Alto, Calif.: HLI034a, HLI0346b). Alternatively, a library can be produced using mucosal scrapings from human colon or intestine. Briefly, total RNA is isolated from the tissue essentially as described by Chirgwin et al. (1979, Biochemistry 18:5294; see also Ausubel et al., supra). An oligo (dT) column is then used to isolate poly(A)$^+$ RNA by the method of Aviv et al. (1972, J. Mol. Biol. 134:743; see also Ausubel et al., supra). Double-stranded cDNA is then produced by reverse transcription using oligo (dT)$_{12-18}$ or random hexamer primers (or both). RNAse H and E. coil DNA poli are then used to replace the RNA strand with a second DNA strand. In a subsequent step E. coli DNA ligase and T4 DNA polymerase are used to close gaps in the second DNA strand and create blunt ends. Generally, the CDNA created is next methylated with EcoRI methylase and EcoRI linkers are added (other linkers can be used depending on the vector to be used). In subsequent steps the excess linkers are removed by restriction digestion and the cDNA fragments are inserted into the desired vector. See Ausubel et al., supra and Sambrook et al. (1990, Molecular Cloning: A Laboratory Manual, Cold Spring Harbor Laboratory Press, Cold Spring Harbor, N.Y.) for detailed protocols. Useful vectors include: λgtll, λgtlO, Lambda ZAP® II vector, Lambda Uni-ZAP® XR vector, all available from Stratagene (La Jolla, Calif.).

The cDNA library must be packaged into phage; this is most readily accomplished by use of a commercial in vitro packaging kit, e.g., Gigapack® II Gold or Gigapack® II Plus (Stratagene, La Jolla, Calif.). See Ausubel et al. (supra) for packaging protocols and suitable host strains. The library is preferably amplified soon after packaging; this step generates sufficient clones for multiple screening of the library. See Ausubel et al. supra or Sambrook et al. supra for details of amplification protocols and procedures for storing the amplified library.

Screening of the cDNA Library

To screen the library it must be placed on an appropriate host strain (e.g., Y1090 or Y1088 for λgtlO libraries, C600hflA for λgtlO libraries). After plating the phage, plaques are transferred to nitrocellulose or nylon filters (See Ausubel et al., supra and Sambrook et al. supra). The filters are then probed with $\alpha^{32}$P-labelled nick translated probe derived from rITF. The probe is preferentially generated using a portion of the region of rITF DNA coding for the trefoil structure (nucleotides 114 to 230 of SEQ ID NO.:1, which encode cys32 to phe71 of SEQ ID NO.:2). This region is conserved between rITF, pS2 and PSP, and it is likely that this region is conserved between rITF and hITF. Once a plaque is identified, several cycles of plaque purification are required to isolate a pure clone encoding hITF. A phage DNA isolation is performed and the cDNA insert can be subcloned into an appropriate vector for restriction mapping and sequencing. If the phage vector is Lambda ZAP® II, coinfection with helper phage allows rescue and recircularization of pBluescript SK⁻ phagemid vector (Stratagene, La Jolla, Calif.) harboring the cDNA; alternatively the phage clone is purified and the cDNA insert is subcloned into a vector suitable for restriction mapping and sequencing. If the clone does not contain the entire hITF gene (as assessed by homology to rITF and the presence of start and stop codons), the library can be rescreened with the original rITF probe or, preferably, with a probe generated from the hITF clone obtained. If none of the clones contain the intact gene, it can be reconstructed from clones which bear overlapping fragments of hITF.

Direct Isolation of an hITF Probe by PCR

It is possible to isolate part of the hITF gene directly from the packaged library or cDNA. To isolate a portion of hITF directly from the packaged library, a pair of oligonucleotide primers and Taq polymerase are used to amplify the DNA corresponding to the hITF gene. The primers used would be approximately 15–20 nucleotides long and correspond in sequence to the 5'-most and 3'-most portions of the rITF coding sequence. Friedman et al. (in PCR Protocols: A Guide to Methods and Applications, Innis et al., Eds., Academic Press, San Diego) describe a procedure for such amplification. Briefly, phage particles are disrupted by heating; Taq polymerase, primers (300 pmol of each), dNTPs, and Taq polymerase buffer are added; and the mixture is thermally cycled to amplify DNA. The amplified DNA is isolated by agarose gel electrophoresis. The ends of the fragment are prepared for ligation into an appropriate vector by making them flush with T4 polymerase and, if desired, adding linkers. Alternatively, a restriction site may be engineered into the fragment by using primers which have sequence added to their 5' ends which sequence will generate an appropriate sticky end when digested. For example the sequence: 5'-GGGCGGCCGC-3' (SEQ ID NO.:4) can be added to the 5' end of each primer. This sequence includes the NotI restriction site flanked at the 5' end by the sequence: GG. The additional nucleotides prevent the 5' ends from denaturing and interfering with subsequent restriction digestion with NotI. The gel purified DNA of the appropriate size is next cloned into a cloning vector for sequencing and restriction mapping. This clone will not have the entire hITF sequence, rather it will be a combination of hITF (the region between the sequences corresponding to the primers) and rITF (the 5' and 3' ends which correspond to the primer sequences). However, this DNA can be used to generate a labelled probe (produced by nick translation or random primer labelling) which, since it is the correct hITF sequence, can be used in a high stringency screening of the library from which the cDNA was originally isolated. In an alternative approach, cDNA can be used in the above procedure instead of a packaged library. This eliminates the steps of modifying the cDNA for insertion into a vector as well as cDNA packaging and library amplification. Ausubel et al. supra provides a protocol for amplification of a particular DNA fragment directly from cDNA and a protocol for amplification from poly(A)$^+$ RNA.

Identification of a Presumptive Human ITF clone

A nick translated probe derived from rITF cDNA (corresponding to nucleotides 1 to 431 of SEQ ID NO.:1) was used for Northern blot analysis of poly(A)$^+$ RNA derived from human intestinal mucosal scrapings. Probe hybridization and blot washing were carried out according to standard procedures. Probe ($5 \times 10^5$ cpm/ml hybridization buffer) was hybridized to the filter at 45° C. in 5X SSC with 30% formamide. The filter was then washed at 60° C. in 5X SSC with 40% formamide. Using this protocol a band was clearly visible after an overnight exposure of the filter with an intensifying screen. This result indicated that there is sufficient homology between rITF and hITF to allow the use of probes derived from the sequence of the rITF gene for identification of the hITF gene.

A human intestinal cDNA library was obtained from Clontech (Palo Alto, Calif.). Alternatively, a human intestinal cDNA library may be produced from mucosal scrapings as described above. Four oligonucleotide probes were selected for screening the library cDNA. Two of the probes correspond to sequences within the region of rITF encoding the trefoil and are referred to as internal probes (5'-GTACATTCTGTCTCTTGCAGA-3' (SEQ ID NO.:5) and 5'-TAACCCTGCTGCTGCTGGTCCTGG-3' (SEQ ID NO.:6). The other two probes recognize sequences within rITF but outside of the trefoil encoding region and are referred to as external probes (5'-GTTTGCGTGCTGCCATGGAGA-3' (SEQ ID NO.:7) and 5'-CCGCAATTAGAACAGCCTTGT-3' (SEQ ID NO.:8). These probes were tested for their utility by using them to screen the rat intestinal cDNA library described above. Each of the four probes could be used to identify a clone harboring all or part of the rITF gene. This result indicates that these probes may be used to screen the human intestinal library for the presence of hITF.

The internal probes were used as described above to amplify a DNA fragment from human colon library cDNA (Clontech, Palo Alto, Calif.). Linkers were added to the isolated DNA fragment which was then inserted into pBluescript phagemid vector (Stratagene, La Jolla, Calif.). The region of this clone corresponding to the sequence of human cDNA (i.e., not including the sequence corresponding to the internal probes) was used to make a radioactively labelled probe by random oligonucleotide-primed synthesis (Ausbel et al., supra). This probe was then used to screen the human colon cDNA library. This screening led to the identification of 29 clones. One of these clones (HuPCR-ITF) was nick-translated to generate a probe for Northern analysis of poly(A)$^+$ RNA isolated from human intestinal mucosal scrapings. A single band of roughly the same size as the rat transcript (approximately 0.45 kDa) was observed.

Northern analysis of poly(A)$^+$ isolated from human tissues indicated that RNA corresponding to this probe was expressed in the small intestine and the large intestine but not in the stomach or the liver. These results indicate that the clone does not encode the human homolog of porcine PSP. Porcine PSP is expressed in porcine pancreas and is not significantly expressed in the small or large intestine. These results also distinguish the cloned gene from pS2 which is expressed in the stomach.

FIG. 6 shows the nucleic acid sequence information for human ITF cDNA, along with the deduced amino acid sequence in one-letter code (SEQ ID NO.:3). This clone was obtained by the methods described above.

Production of hITF

The isolated hITF gene can be cloned into a mammalian expression vector for protein expression. Appropriate vectors include pMAMneo (Clontech, Palo Alto, Calif.) which provides a RSV-LTR enhancer linked to a dexamethasone-inducible NMT-LTR promoter, an SV40 origin of replication (allows replication in COS cells), a neomycin gene, and SV40 splicing and polyadenylation sites. This vector can be used to express the protein in COS cells, CHO cells, or mouse fibroblasts. The gene may also be cloned into a vector for expression in drosophila cells using the bacoluvirus expression system.

Purification of Intestinal Trefoil Factor

Intestinal trefoil factor can be purified from intestinal mucosal scrapings of human, rats or any other species which expresses ITF (pigs and cows may provide a source of ITF). The purification procedure used for PSP will be useful for the purification of ITF since the proteins are likely to be homologous. Jorgensen et al. describes a method for purification of PSP (1982, Regulatory Peptides 3:207). The preferred method is the second approach described by Jorgensen et al. (supra). This method involves chromatography of SP-Sephadex C-25 and QAE Sephadex A-25 columns (Sigma, St. Louis, Mo.) in acidic buffer.

Anti-Intestinal Trefoil Factor Monoclonal Antibodies

Anti-intestinal trefoil factor monoclonal antibodies can be raised against synthetic peptides whose sequences are based on the deduced amino acid sequence of cloned hITF (SEQ ID NO.:3). Most commonly the peptide is based on the amino- or carboxy-terminal 10–20 amino acids of the protein of interest (here, hITF). The peptide is usually chemically cross-linked to a carrier molecule such as bovine serum albumin or keyhole limpet hemocyanin. The peptide is selected with the goal of generating antibodies which will cross-react with the native hITF. Accordingly, the peptide should correspond to an antigenic region of the peptide of interest. This is accomplished by choosing a region of the protein which is (1) surface exposed, e.g., a hydrophobic region or (2) relatively flexible, e.g., a loop region or a β-turn region. In any case, if the peptide is to be coupled to a carrier, it must have an amino acid with a side chain capable of participating in the coupling reaction. See Hopp et al. (1983, Mol. Immunol. 20:483; 1982, J. Mol. Biol. 157:105) for a discussion of the issues involved in the selection of antigenic peptides. A second consideration is the presence of a protein homologous to hITF in the animal to be immunized. If such a protein exists, it is important to select a region of hITF which is not highly homologous to that homolog.

For hITF, peptides that correspond to the amino-terminal or carboxy-terminal 15 amino acids are likely to be less homologous across species and exposed to the surface (and thus antigenic). Thus they are preferred for the production of monoclonal antibodies. Purified hITF can also be used for the generation of antibodies.

Genetic Disruption of a Trefoil Protein Impairs the Defense of Intestinal Mucosa As stated above, ITF is a member of the family of trefoil proteins that are expressed specifically and abundantly at the mucosal surface of the gastrointestinal tract. Other members of this family include pS2, which is expressed almost exclusively by foveolar cells of the stomach (Masiakowski et al., 1982, Nucl. Acids. Res. 10:7896; Jorgensen et al., 1982, Regulatory Peptides 3:231), and pancreatic spasmolytic peptide (SP), which is expressed by the pancreas and by gastric antrui (Jorgensen et al., supra). As described above, the expression of these proteins is enhanced in the proximity of the injured bowel.

In order to study the role of ITF in vivo, the gene was rendered non-functional by targeted disruption in mice.

Isolation of the Murine ITF Gene and Generation of ITF-Deficient Mice

The murine ITF gene was isolated from a phage genomic library using the rat ITF cDNA sequence as a probe, and its identity was confirmed by nucleotide sequencing using standard techniques (Mashimo et al., 1995, Biochem. Biophys. Res. Comm. 210:31).

Figure 7:
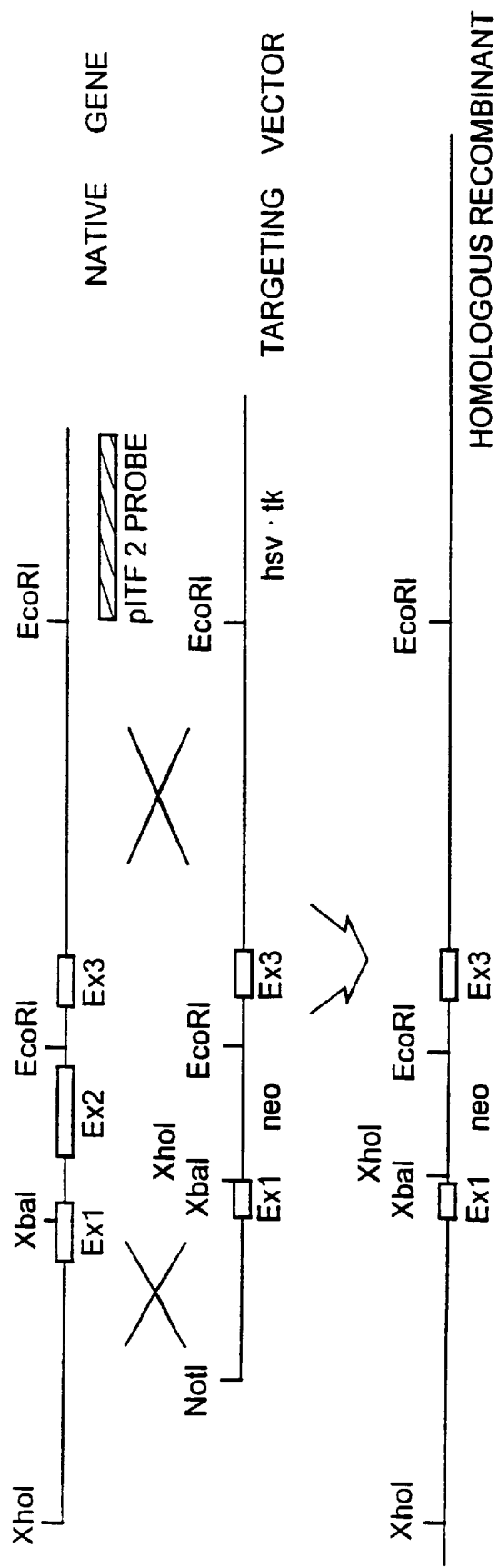
FIG. 7 is a diagram depicting the strategy used to mutate the ITF gene in embryonic stem cells.

A targeting vector for disrupting the gene by homologous recombination in embryonic stem (ES) cells was designed and constructed, as shown in FIG. 7. The entire second exon (Ex2) of the murine ITF gene, which is contained within the XbaI-EcoRI fragment shown, was replaced with the neomycin resistance (neo) gene cassette. As the deleted sequence encodes most of the "trefoil domain", the ability of any resultant peptides to produce the looping structure characteristic of trefoil proteins is abolished. A positive-negative selection strategy (Mansour et al., 1988, Nature 336:348) was used to enrich for homologous recombination events in the embryonic stem (ES) cells by selecting for neo within the homologous DNA and against a herpes simplex virus thymidine kinase gene (hsv-tk) placed at the 3' end of the targeting vector. The pPNT plasmid (Tybulewicz et al., 1991, Cell 65:1153) was used to construct the targeting vector. The targeting vector was linearized with the restriction enzyme NotI and electroporated into pluripotent J1 ES cells (Li et al., 1992, Cell 69:915) under conditions previously described (Strittmatter et al., 1995, Cell 80:445). Disruption of the ITF gene in ES cells following homologous recombination was distinguished from random integration of the targeting vector by Southern blot analysis of genomic DNA from individual clones of cells digested with the restriction enzyme XhoI. The pITF2 probe identified a 19 kb "wild type" fragment and a 23 kb "knock out" fragment created by introduction of an XhoI site upon homologous insertion of the targeting vector. Approximately 10% of neomycin-resistant ES clones were found to have undergone homologous ITF recombination using this method.

The polymerase chain reaction (PCR) was used to confirm the targeted mutation as follows. A 200 bp region of DNA was amplified using primers spanning exon 2 of ITF (5'-GCAGTGTAACAACCGTGGTTGCTGC-3' (SEQ ID NO.:9) and 5'-TGACCCTGTGTCATCACCCTGGC-3' (SEQ ID NO.:10)); and a 400 bp region of the neo gene was amplified with a second set of primers (5'-CGGCTGCTCTGATGGCCGCC-3' (SEQ ID NO.:11) and 5'-GCCGGCCACAGTCGATGAATC-3' (SEQ ID NO.:12) The DNA template for the PCR reaction was obtained from tail tissue. Approximately 0.5 cm of the tail was cut off each animal, and the samples were digested with proteinase-K (200 µl at 0.5 mg/ml in 50 m Tris-HCl pH 8.0 and 0.5% Triton X-100; Sigma, St. Louis, Mo.) at 55° C. overnight. One µl of this mixture was added directly to a 25 µl PCR reaction (per Stratagene, Menosha, Wis.). The reaction was begun with a "hot start" (incubation at 96° C. for 10 minutes), and the following cycle was repeated 30 times: 72° C. for 120 seconds (hybridization and elongation) and 96° C. for 30 seconds (denaturation). Ten µl of each reaction mixture was electrophoresed on a 2% agarose gel. Wild type animals were identified by the presence of a 200 bp fragment, corresponding to an intact ITF gene, heterozygous animals were identified by the presence of this band and, in addition, a 400 bp fragment produced by amplification of the neo gene, and ITF-deficient (knock out) animals were identified by the presence of only the fragment corresponding to the neo gene.

Two ES clones, which arose independently, were used to derive two lines of mice lacking ITF. These mice were screened by Southern genomic blot analysis as described for ES clones, or by PCR.

Analysis of Trefoil Peptide Expression in Wild Type and Mutant Mice

Although expression of ITF is abolished in the mutant mice, expression of other trefoil genes is preserved.

Northern blot analysis was performed using cDNA probes for ITF (Suemori et al., 1991, Proc. Natl. Acad. Sci. USA 88:11017), SP (Jeffrey et al., 1994 Gastroenterology 106:336), and, as a positive control, glyceraldehyde 3-phosphate dehydrogenase (GAPDH). The nucleic acid probe for murine pS2 was made by reverse transcription-polymerase chain reaction (RT-PCR) using the oligonucleotide pairs: 5'-GAGAGGTTGCTGTTTTGATGACA-3' (SEQ ID NO.:13) and 5'-GCCAAGTCTTGATGTAGCCAGTT-3" (SEQ ID NO.:14), which were synthesized based on the published mouse pS2 cDNA sequence (GenBank Accession Number: Z21858). The GeneAmp RNA PCR Kit (Perkin Elmer) was used according to the manufacturer's instructions, as was the pCR™II (Invitrogen) cloning vector. RNA was extracted from the following tissues from both wild type and ITF-deficient (knock out) mice: stomach, duodenum, terminal ileum, right colon, appendix, transverse colon, left colon, and rectum. Fifteen µg of total RNA from each sample were electrophoresed on a 1% agarose gel, and transferred to nitrocellulose paper. Following hybridization, washing, and autoradiography, wild type mice exhibited a pattern of tissue expression considered normal: ITF was expressed in the small intestine and colon, which is the same expression pattern seen for ITF in the rat and human. The analysis of mutant mice confirmed the lack of ITF expression in the gastrointestinal tract. In contrast, the expression of the other trefoil proteins, SP and pS2, are unaltered in the gastrointestinal tract of mutant mice. SP was expressed in the stomach and, at lower levels, in the duodenum of both wild type and mutant mice. Similarly, pS2 was expressed in the stomach of both wild type and ITF-deficient mice.

Immunocytochemistry Reveals that ITF is not Expressed in the Colon of ITF-deficient mice In order to confirm that ITF protein was not expressed by ITF knock out mice, immunocytochemistry was performed as follows. Tissue from the colon and small intestine was fixed in the course of perfusion, immersed in 4% paraformaldehyde (McLean et al., 1974, J. Histochem. Cytochem. 22:1077), and embedded in paraffin. Sections were collected and stained either with a polyclonal antibody raised against a synthetic peptide from the predicted 18 carboxy-terminal amino acids of murine ITF or a monoclonal antibody against colonic mucin (Podolsky et al., 1986, J. Clin. Invest. 77:1263). Primary antibody binding was visualized with a biotinylated secondary antibody, Avidin DH, biotinylated horseradish peroxidase H, and diaminobenzidine tetrahydrochloride reagents according to the manufacturer's instructions (VectaStain ABC, Vector Laboratories, Bulingame, Calif.). Following immunocytochemistry, the sections were counterstained with hematoxylin and viewed. Goblet cells in the colon of wild type mice were immunoreactive with both antibodies, staining positively for ITF and mucin. In contrast, the goblet cells in the colon of ITF-deficient mice lacked detectable ITF but continued to express colonic mucin.

Induction of Mild Colonic Boithelial Injury with Dextran Sulfate Sodium

ITF-deficient mice derived from each ES clone appear to develop normally and are grossly indistinguishable from heterozygous and wild type litter mates. Their growth is not retarded and they reach maturity without evident diarrhea or occult fecal blood loss. However, the colon of ITF-deficient mice may be more prone to injury than the colon of wild type mice. To investigate this hypothesis, dextran sulfate sodium (DSS), which reproducibly creates mild colonic epithelial injury with ulceration in mice (Kim et al., 1992, Scand. J. Gastroent. 27:529; Wells et al., 1990, J. Acquired Immune Deficiency Syndrome 3:361; Okayasu et al., 1990, Gastroenterology 98:694) was administered in the animals' drinking water. After standardization of DSS effects in comparable wild type mice, a group of 20 wild type and 20 ITF-deficient mice (litter mates from heterozygous crosses, weighing>20 grams each) were treated with 2.5% DSS in their drinking water for nine days.

Figure 8:
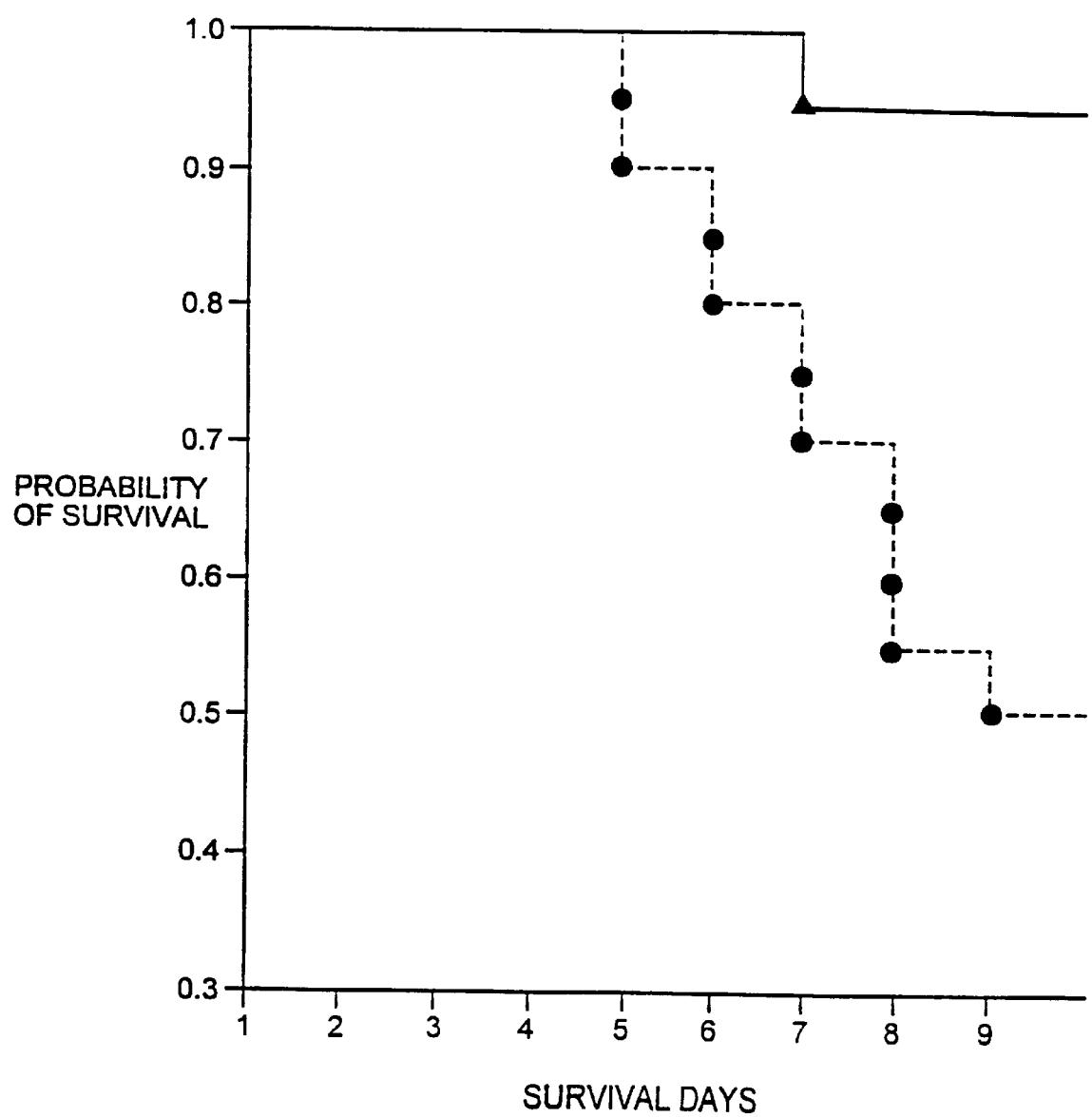
FIG. 8 is a graph depicting survival following administration of Dextran Sulfate Sodium (DSS; 2.5% w/v in drinking water for 9 consecutive days), shown as Kaplan-Meier transform of probability versus days of DSS treatment.

Although 85% of wild type mice and 100% of ITF-deficient mice treated with DSS demonstrate occult blood (using Hemoccult, Smith Kline Diagnostics, San Jose, Calif.) in their stool during the period of treatment, ITF-deficient mice were markedly more sensitive to the injurious effects of DSS. Fifty percent of ITF-deficient mice developed frankly bloody diarrhea and died (FIG. 8). In contrast, only 10% of wild type mice treated similarly exhibited bloody diarrhea, and only 5% died. Weight loss was also significantly more pronounced in ITF-deficient mice than wild type mice receiving DSS.

ITF-Deficient Mice Treated with Dextran Sulfate Sodium (DSS) Develop Severe Colonic Erosions After seven days of treatment with DSS (2.5% w/v), the colons of wild type and ITF-deficient mice were examined histologically. Left colon transections were fixed in 4% paraformaldehyde, mounted in paraffin, and stained with hematoxylin and eosin. Multiple sites of obvious ulceration and hemorrhage were present in the colon of ITF-deficient mice, while the colons of most wild type mice were grossly indistinguishable from those of untreated mice. Histological examination of the DSS-treated ITF-deficient colon confirmed the presence of multiple erosions and intense inflammatory changes including crypt abscesses. Damage was more pronounced in the distal colon, i.e., the descending colon, sigmoid colon, and rectum, which contained large, broad areas of mucosal ulceration. When similarly inspected, mucosal erosions could be seen in the tissue of 80% of the DSS-treated wild type mice, but most were small lesions that also appeared to be healing, with complete re-epithelialization of most lesions. There was no evidence of re-epithelialization in the colons of ITF-deficient mice exposed to DSS.

During the normal course of growth and development, intestinal epithelial cells originate from stem cells in the intestinal crypts and rapidly progress up the crypt and villus to be extruded from the villus tip within five days. After intestinal injury, the epithelial covering is repopulated by cells which appear to generate signals to heal the lesion by modulation of epithelial and mesenchymal cell growth and matrix formation (Poulsom et al., 1993, J. Clin. Gastroenterol. 17:S78). In vitro evidence suggests that trefoil proteins play a key role in re-establishing mucosal integrity after injury. Despite the normal restriction of SP and pS2 expression to the proximal gastrointestinal tract, these trefoil proteins and ITF are abundantly expressed at sites of colonic injury and repair.

The DSS model described above provides a system for testing the protective effects of ITF, other trefoil peptides, or active polypeptide fragments or variants thereof. One can administer a molecule to be tested to DSS-treated mice, either wild type or ITF-deficient mice, and determine whether the molecule has therapeutic effects by performing the assays described above.

In addition to the use of DSS, any chemical compound that is known to damage the mucosa lining the digestive tract can be used to assay the proteins of the invention. These compounds include, but are not limited to, alcohol, indomethacin, and methotrexate. For example, methotrexate (MTX) can be administered intraperitoneally to mice at a dose of 40 mg/kg. One group of MTX-treated animals could be given, in addition, the protein in question. Various parameters, such as body weight, the presence of lesions in the digestive tract, and mortality of these animals could then be compared to equivalent measurements taken from animals that were not treated with the protein.

In Situ *H. pylori* Binding Assay

One method for determining whether a given protein (or protein fragment or variant) is useful in the prevention or treatment of diseases associated with *H. pylori* infection is to examine it in the context of an established animal model of *H. pylori* infection. One such model was recently developed by Falk et al. (1995, Proc. Natl. Acad. Sci. USA 92:1515–1519). This model involves the use of transgenic mice that express the enzyme α-1,¾-fucosyltransferase and, as a consequence, express $Le^b$ on the surface of mucosal cells that bound clinical isolates of *H. pylori*. If the addition of a protein, such as ITF, to this system reduces the level of *H. pylori* binding to the mucosal cell, the protein would be considered an inhibitor of *H. pylori*. More specifically, the assay could be carried out as follows. *H. pylori* are obtained, for example, from patients with gastric ulcers or chronic active gastritis, grown to stationary phase, and labeled, for example with digoxigenin or fluorescein isothiocyanate (FITC). The labeled bacteria are then exposed, together with the protein of interest, to frozen sections prepared from the stomach, duodenum, ileum, or liver of adult transgenic mice (as described above). As a control, the experiment could be performed in parallel using tissue from a wild type littermate. The sections are fixed with ice-cold methanol for 5 minutes, rinsed three times with wash buffer (TBS; 0.1 mM $CaCl_2$, 1 mM $MnCl_2$, 1 mM $MgCl_2$; 10 minutes/cycle), and treated with blocking buffer (Boehringer Mannheim; see also Falk supra). Bacteria are diluted to an $OD_{600}$ of 0.05 with dilution buffer (TBS; 0.1 mM $CaCl_2$, 1 mM $MnCl_2$, 1 mM $MgCl_2$ containing leupeptin (1 µg/ml), aprotinin (1 µg/ml), [-1-p-tosylamido-2-phenylethyl chloromethyl ketone (100 µg/ml), phenylmethylsulfonyl fluoride (100 µg/ml), and pepstatin A (1 µg/ml)] and overlaid on the sections for 2 hours at room temperature in a humidified chamber. Slides are then washed six times in wash buffer on a rotating platform (5 minutes/cycle at room temperature). Digoxigenin-labeled bacteria are visualized on washed slides with FITC-conjugated sheep anti-digoxigenin immunoglobulin (Boehringer Mannheim) diluted 1:100 in histoblocking buffer. Nuclei were stained with bisbenzimide (Sigma). For blocking controls, digoxigenin-conjugated stationary-phase bacteria can be suspended in dilution buffer to an $OD_{600}$ of 0.05 and shaken with or without $Le^b$-HSA or $Le^a$-HSA (final concentration, 50 µg/ml; reaction mixture, 200 µl) for 1 hour at room temperature. The suspension is then overlaid on methanol-fixed frozen sections.

Use

In the practice of the present invention, ITF may be administered orally, intravenously, or intraperitoneally for treatment of peptic ulcer diseases, inflammatory bowel diseases, and for protection of the intestinal tract from injury caused by bacterial infection, radiation injury or other insults. The mode of administration, dosage, and formulation of ITF will depend upon the condition being treated.

Skilled pharmacologists are able to readily determine appropriate dosage regimens. As trefoil peptides are not degraded within the digestive tract, it is expected that the route of administration will be oral, and that the dosage will range from 1 to 500 mg, taken once to three times per day. The peptide could be administered, for example, in the form of a tablet, capsule, or pill, or could be suspended in a solution, such as a syrup, that the patient swallows. Alternatively, the solution containing the peptide may be administered as a gastric lavage. The peptide may also be included in a solution that is administered as an enema, or it may be administered as a suppository.

Deposit Statement

The human intestinal trefoil clone described herein has been deposited under conditions in which access will be available during the pendency of the present patent application to those determined by the Commissioner of Patents and Trademarks to be entitled thereto under 37 C.F.R. § 1.14 and 35 U.S.C. § 122. More specifically, the human intestinal trefoil clone described herein has been deposited with the American Type Culture Collection (Manassas, Va.) and assigned Accession Number 98767.

Other Embodiments

ITF may be used to produce monoclonal antibodies for the detection of ITF in intestinal tissue or blood serum by means of an indirect immunoassay. ITF may be detectably labelled and used in an in situ hybridization assay for the detection of ITF binding sites. Labels may include, but are not limited to, fluorescein or a radioactive ligand.

ITF may be used to protect and stabilize other proteins. This protection is accomplished by forming a hybrid molecule in which all or part of ITF is fused to either the carboxy-terminus or the amino-terminus (or both) of the protein of interest. Because ITF is resistant to degradation in the digestive system, it will protect the protein of interest from such degradation. As a consequence, the protein of interest is likely to remain active in the digestive system and/or will be more readily absorbed in an intact form.

Trefoil proteins, including ITF, can be used to promote healing or prevent wounding of corneal tissue.

Stably dimerized trefoil protein can be used in the methods of the invention. Such molecules can be prepared by stably crosslinking monomers of trefoil or by expressing a gene encoding a tandem repeat of a trefoil protein (e.g., ITF) or a portion thereof (e.g., a portion capable of forming the three loop structure characteristic of trefoil proteins).

Also useful in the method of the invention are trefoil proteins produced by chemical synthesis.

Trefoil proteins can be used to treat other disorders, e.g., Crohn's disease.

Other embodiments are within the following claims.

What is claimed is:

1. A method for treating digestive disorders in a human patient, the method comprising administering to the patient a therapeutic composition comprising a substantially pure polypeptide comprising the amino acid sequence encoded by the cDNA deposited with the American Type Culture Collection and assigned Accession Number 98767 (intestinal trefoil factor) and a pharmacologically acceptable carrier.

2. A method for the treatment of lesions in the alimentary canal of a patient, the method comprising administering to the patient a polypeptide comprising the amino acid sequence encoded by the cDNA clone deposited with the American Type Culture Collection and assigned Accession Number 98767 (intestinal trefoil factor).

3. The method of claim 2, wherein the lesion is in the mucosa of the alimentary canal.

4. The method of claim 2, wherein the lesion is in the mouth of the patient.

5. The method of claim 2, wherein the lesion is in the esophagus of the patient.

6. The method of claim 2, wherein the lesion is in the stomach of the patient.

7. The method of claim 2, wherein the lesion is in the intestine of the patient.

8. The method of claim 2, wherein the patient is receiving radiation therapy for the treatment of cancer.

9. The method of claim 2, wherein the patient is receiving chemotherapy for the treatment of cancer.

10. The method of claim 2, wherein the patient is receiving a drug that damages the alimentary canal.

11. The method of claim 2, wherein the patient is suffering from a digestive disorder.

12. The method of claim 11, wherein the digestive disorder is non-ulcer dispepsia.

13. The method of claim 11, wherein the digestive disorder is gastritis.

14. The method of claim 11, wherein the digestive disorder is gastro-esophageal reflux disease.

15. The method of claim 11, wherein the digestive disorder is a peptic ulcer or duodenal ulcer.

16. The method of claim 2, wherein the administration is oral.

17. The method of claim 2, wherein the administration further comprises administration of mucin glycoprotein preparations.

* * * * *

UNITED STATES PATENT AND TRADEMARK OFFICE
CERTIFICATE OF CORRECTION

PATENT NO.    : 6,221,840 B1
DATED         : April 24, 2001
INVENTOR(S)   : Daniel K. Podolsky It is certified that error appears in the above-identified patent and that said Letters Patent is hereby corrected as shown below:

<u>Title page,</u>
Item [56], OTHER PUBLICATIONS, change "Nucleic Acis Res." to -- Nucleic Acid Res. --;

<u>Column 3,</u>
Line 39, after "macromolecule." start new paragraph;

<u>Column 4,</u>
Line 33, change "used promote" to -- used to promote --;

<u>Column 6,</u>
Line 27, change "rITE" to -- rITF --;

<u>Column 7,</u>
Line 32, change "immunofluoresce" to -- immunofluorescence --;

<u>Column 8,</u>
Line 1, change "poli" to -- polI --;
Line 5, change "CDNA" to -- cDNA --;
Line 14, change "Uni-ZAP®" to -- Uni-ZAP$^{TM}$ --;

<u>Column 10,</u>
Line 37, change "NMT-LTR" to -- MMTV-LTR --;

<u>Column 11,</u>
Line 31, change "antrui" to -- antrum --;

UNITED STATES PATENT AND TRADEMARK OFFICE
CERTIFICATE OF CORRECTION

PATENT NO. : 6,221,840 B1
DATED : April 24, 2001
INVENTOR(S) : Daniel K. Podolsky It is certified that error appears in the above-identified patent and that said Letters Patent is hereby corrected as shown below:

Column 12,
Line 16, change ":12)" to -- :12)) --;
Line 20, change "50 m" to -- 50mM --;

Column 13,
Line 32, change "Boithelial" to -- Epithelial --.

Signed and Sealed this

Twenty-fifth Day of March, 2003

JAMES E. ROGAN
*Director of the United States Patent and Trademark Office*

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 431 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 18...260

(xi) SEQUENCE DESCRIPTION: SEQ ID NO: 1:

```
GAAGTTTGCG TGCTGCC ATG GAG ACC AGA GCC TTC TGG ATA ACC CTG CTG        50
                   Met Glu Thr Arg Ala Phe Trp Ile Thr Leu Leu
                    1               5                      10

CTG GTC CTG GTT GCT GGG TCC TCC TGC AAA GCC CAG GAA TTT GTT GGC        98
Leu Val Leu Val Ala Gly Ser Ser Cys Lys Ala Gln Glu Phe Val Gly
             15                  20                  25

CTA TCT CCA AGC CAA TGT ATG GCG CCA ACA AAT GTC AGG GTG GAC TGT       146
Leu Ser Pro Ser Gln Cys Met Ala Pro Thr Asn Val Arg Val Asp Cys
         30                  35                  40

AAC TAC CCC ACT GTC ACA TCA GAG CAG TGT AAC AAC CGT GGT TGC TGT       194
Asn Tyr Pro Thr Val Thr Ser Glu Gln Cys Asn Asn Arg Gly Cys Cys
     45                  50                  55

TTT GAC TCC AGC ATC CCA AAT GTG CCC TGG TGC TTC AAA CCT CTG CAA       242
Phe Asp Ser Ser Ile Pro Asn Val Pro Trp Cys Phe Lys Pro Leu Gln
 60                  65                  70                  75

GAG ACA GAA TGT ACA TTT TGAAGCTGTC CAGGCTCCAG GAAGGGAGCT CCACACCC     298
Glu Thr Glu Cys Thr Phe
                     80

TGGACTCTTG CTGATGGTAG TGGCCCAGGG TAACACTCAC CCCTGATCTG CTCCCTCGCG     358

CCGGCCAATA TAGGAGCTGG GAGTCCAGAA GAATAAAGAC CTTACAGTCA GCACAAGGCT     418

GTTCTAATTG CGG                                                        431
```

(2) INFORMATION FOR SEQ ID NO: 2:

(i) SEQUENCE CHARACTERISTICS:
        (A) LENGTH: 81 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 2:

```
Met Glu Thr Arg Ala Phe Trp Ile Thr Leu Leu Val Leu Val Ala
 1               5                  10                  15

Gly Ser Ser Cys Lys Ala Gln Glu Phe Val Gly Leu Ser Pro Ser Gln
                 20                  25                  30

Cys Met Ala Pro Thr Asn Val Arg Val Asp Cys Asn Tyr Pro Thr Val
             35                  40                  45

Thr Ser Glu Gln Cys Asn Asn Arg Gly Cys Cys Phe Asp Ser Ser Ile
         50                  55                  60

Pro Asn Val Pro Trp Cys Phe Lys Pro Leu Gln Glu Thr Glu Cys Thr
 65                  70                  75                  80

Phe
```

(2) INFORMATION FOR SEQ ID NO: 3:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 2...223

(xi) SEQUENCE DESCRIPTION: SEQ ID NO: 3:

```
G ATG CTG GGG CTG GTC CTG GCC TTG CTG TCC TCC AGC TCT GCT GAG GAG     49
```

```
    Met Leu Gly Leu Val Leu Ala Leu Leu Ser Ser Ser Ala Glu Glu
      1               5                  10                  15

TAC GTG GGC CTG TCT GCA AAC CAG TGT GCC GTG CCG GCC AAG GAC AGG         97
Tyr Val Gly Leu Ser Ala Asn Gln Cys Ala Val Pro Ala Lys Asp Arg
                 20                  25                  30

GTG GAC TGC GGC TAC CCC CAT GTC ACC CCC AAG GAG TGC AAC AAC CGG        145
Val Asp Cys Gly Tyr Pro His Val Thr Pro Lys Glu Cys Asn Asn Arg
         35                  40                  45

GGC TGC TGC TTT GAC TCC AGG ATC CCT GGA GTG CCT TGG TGT TTC AAG        193
Gly Cys Cys Phe Asp Ser Arg Ile Pro Gly Val Pro Trp Cys Phe Lys
         50                  55                  60

CCC CTG CAG GAA GCA GAA TGC ACC TTC TGAGGCACCT CCAGCTGCCC CTG          243
Pro Leu Gln Glu Ala Glu Cys Thr Phe
 65                  70

GGATGCAGGC TGAGCACCCT TGCCCGGCTG TGATTGCTGC CAGGCACTGT TCATCTCAGT      303

TTTTCTGTCC CTTTGCTCCC GGCAAGCTTT CTGCTGAAAG TTCATATCTG GAGCCTGATG      363

TCTTAACGAA TAAAGGTCCC ATGCTCCACC CGAAAAA                               400

(2) INFORMATION FOR SEQ ID NO: 4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 4:

GGGCGGCCGC                                                              10

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 5:

GTACATTCTG TCTCTTGCAG A                                                 21

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 6:

TAACCCTGCT GCTGCTGGTC CTGG                                              24

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 7:

GTTTGCGTGC TGCCATGGAG A                                                 21

(2) INFORMATION FOR SEQ ID NO: 8:
```

(i) SEQUENCE CHARACTERISTICS:
      (A) LENGTH: 21 base pairs
      (B) TYPE: nucleic acid
      (C) STRANDEDNESS: single
      (D) TOPOLOGY: linear (xi) SEQUENCE DESCRIPTION: SEQ ID NO: 8:

CCGCAATTAG AACAGCCTTG T                                                       21

(2) INFORMATION FOR SEQ ID NO: 9:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO: 9:

GCAGTGTAAC AACCGTGGTT GCTGC                                                   25

(2) INFORMATION FOR SEQ ID NO: 10:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO: 10:

TGACCCTGTG TCATCACCCT GGC                                                     23

(2) INFORMATION FOR SEQ ID NO: 11:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO: 11:

CGGCTGCTCT GATGGCCGCC                                                         20

(2) INFORMATION FOR SEQ ID NO: 12:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (xi) SEQUENCE DESCRIPTION: SEQ ID NO: 12:

GCCGGCCACA GTCGATGAAT C                                                       21

(2) INFORMATION FOR SEQ ID NO: 13:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO: 13:

GAGAGGTTGC TGTTTTGATG ACA                                                     23

(2) INFORMATION FOR SEQ ID NO: 14:

```
    (i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 14:

GCCAAGTCTT GATGTAGCCA GTT                                               23

(2) INFORMATION FOR SEQ ID NO: 15:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO: 15:

Glu Ala Gln Thr Glu Thr Cys Thr Val Ala Pro Arg Glu Arg Gln Asn
  1               5                  10                  15

Cys Gly Phe Pro Gly Val Thr Pro Ser Gln Cys Ala Asn Lys Gly Cys
             20                  25                  30

Cys Phe Asp Asp Thr Val Arg Gly Val Pro Trp Cys Phe Tyr Pro Asn
         35                  40                  45

Thr Ile Asp Val Pro Pro Glu Glu Glu Cys Glu Phe
     50                  55                  60

(2) INFORMATION FOR SEQ ID NO: 16:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO: 16:

Glu Lys Pro Ala Ala Cys Arg Cys Ser Arg Gln Asp Pro Lys Asn Arg
  1               5                  10                  15

Val Asn Cys Gly Phe Pro Gly Ile Thr Ser Asp Gln Cys Phe Thr Ser
             20                  25                  30

Gly Cys Cys Phe Asp Ser Gln Val Pro Gly Val Pro Trp Cys Phe Lys
         35                  40                  45

Pro Leu Pro Ala Gln Glu Ser Glu Glu Cys Val Met Glu Val
     50                  55                  60

(2) INFORMATION FOR SEQ ID NO: 17:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO: 17:

Gln Glu Phe Val Gly Leu Ser Pro Ser Gln Cys Met Ala Pro Thr Asn
  1               5                  10                  15

Val Arg Val Asp Cys Asn Tyr Pro Thr Val Thr Ser Glu Gln Cys Asn
             20                  25                  30

Asn Arg Gly Cys Cys Phe Asp Ser Ser Ile Pro Asn Val Pro Trp Cys
         35                  40                  45
```

```
Phe Lys Pro Leu Gln Glu Thr Glu Cys Thr Phe
    50                  55
```

(2) INFORMATION FOR SEQ ID NO: 18:

(i) SEQUENCE CHARACTERISTICS:
        (A) LENGTH: 73 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 18:

```
Met Leu Gly Leu Val Leu Ala Leu Leu Ser Ser Ser Ala Glu Glu
 1               5                  10                  15

Tyr Val Gly Leu Ser Ala Asn Gln Cys Ala Val Pro Ala Lys Asp Arg
                20                  25                  30

Val Asp Cys Gly Tyr Pro His Val Thr Pro Lys Glu Cys Asn Asn Arg
            35                  40                  45

Gly Cys Cys Phe Asp Ser Arg Ile Pro Gly Val Pro Trp Cys Phe Lys
        50                  55                  60

Pro Leu Gln Glu Ala Glu Cys Thr Phe
65                  70
```

(2) INFORMATION FOR SEQ ID NO: 19:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO: 19:

```
Glu Ala Gln Thr Glu Thr Cys Thr Val Ala Pro Arg Glu Arg Gln Asn
 1               5                  10                  15

Cys Gly Phe Pro Gly Val Thr Pro Ser Gln Cys Ala Asn Lys Gly Cys
                20                  25                  30

Cys Phe Asp Asp Thr Val Arg Gly Val Pro Trp Cys Phe Tyr Pro Asn
            35                  40                  45

Thr Ile Asp Val Pro Pro Glu Glu Glu Cys Glu Phe
        50                  55                  60
```

(2) INFORMATION FOR SEQ ID NO: 20:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 20:

```
Glu Lys Pro Ala Ala Cys Arg Cys Ser Arg Gln Asp Pro Lys Asn Arg
 1               5                  10                  15

Val Asn Cys Gly Phe Pro Gly Ile Thr Ser Asp Gln Cys Phe Thr Ser
                20                  25                  30

Gly Cys Cys Phe Asp Ser Gln Val Pro Gly Val Pro Trp Cys Phe Lys
            35                  40                  45

Pro Leu Pro Ala Gln Glu Ser Glu Glu Cys Val Met Gln Val Ser Ala
50                  55                  60
```

-continued

```
Arg Lys Asn Cys Gly Tyr Pro Gly Ile Ser Pro Glu Asp Cys Ala Ala
 65              70              75              80

Arg Asn Cys Cys Phe Ser Asp Thr Ile Pro Glu Val Pro Trp Cys Phe
             85              90              95

Phe Pro Met Ser Val Glu Asp Cys His Tyr
            100             105
```